United States Patent
Markosyan

(10) Patent No.: US 10,815,261 B2
(45) Date of Patent: Oct. 27, 2020

(54) COMPOUNDS PRODUCED FROM STEVIA AND PROCESS FOR PRODUCING THE SAME

(71) Applicant: PureCircle Sdn Bhd, Negeri Sembilan (MY)

(72) Inventor: Avetik Markosyan, Kuala Lumpur (MY)

(73) Assignee: PureCircle Sdn Bhd, Negeri Sembilan (MY)

( * ) Notice: Subject to any disclaimer, the term of this patent is extended or adjusted under 35 U.S.C. 154(b) by 0 days.

(21) Appl. No.: 15/300,779

(22) PCT Filed: Apr. 2, 2014

(86) PCT No.: PCT/MY2014/000050
§ 371 (c)(1),
(2) Date: Sep. 29, 2016

(87) PCT Pub. No.: WO2015/152707
PCT Pub. Date: Oct. 8, 2015

(65) Prior Publication Data
US 2017/0022240 A1    Jan. 26, 2017

(51) Int. Cl.
| | | |
|---|---|---|
| *C07H 15/24* | (2006.01) | |
| *C07H 1/06* | (2006.01) | |
| *A61K 47/26* | (2006.01) | |
| *A61K 8/60* | (2006.01) | |
| *A23L 33/10* | (2016.01) | |
| *A23L 2/60* | (2006.01) | |
| *A23L 27/30* | (2016.01) | |
| *A61Q 19/00* | (2006.01) | |
| *C07H 1/00* | (2006.01) | |
| *A61K 36/28* | (2006.01) | |

(52) U.S. Cl.
CPC ............... *C07H 15/24* (2013.01); *A23L 2/60* (2013.01); *A23L 27/33* (2016.08); *A23L 27/36* (2016.08); *A23L 33/10* (2016.08); *A61K 8/602* (2013.01); *A61K 36/28* (2013.01); *A61K 47/26* (2013.01); *A61Q 19/00* (2013.01); *C07H 1/00* (2013.01); *C07H 1/06* (2013.01); *A23V 2002/00* (2013.01); *A61K 2800/10* (2013.01)

(58) Field of Classification Search
CPC ........ A61K 36/26; A61K 47/26; A61K 8/602; A61K 1800/10; C07H 1/00; C07H 15/24; C07H 1/06; A23L 27/36; A23L 2/60; A23L 27/33; A23L 33/10; A23V 2002/00; A61Q 19/00
USPC .......................................................... 514/34
See application file for complete search history.

(56) References Cited

U.S. PATENT DOCUMENTS

| | | | | |
|---|---|---|---|---|
| 4,892,938 A | * | 1/1990 | Giovanetto | A61K 36/28 |
| | | | | 536/127 |
| 2009/0074935 A1 | * | 3/2009 | Lee | C07C 62/32 |
| | | | | 426/548 |
| 2011/0251381 A1 | * | 10/2011 | Lee | C07C 62/32 |
| | | | | 536/18.1 |

FOREIGN PATENT DOCUMENTS

| | | | |
|---|---|---|---|
| EP | 2190854 B1 | † | 11/2011 |
| WO | 2011112892 A1 | † | 9/2011 |
| WO | WO 2011/112892 A1 | * | 9/2011 ............. A61K 31/70 |
| WO | WO 2013/036767 A1 | | 3/2013 |

OTHER PUBLICATIONS

Upreti et al, Int. J. Mol. Sci, 2011, 12(11), 7529-53.*
Valencia et al, Bioresource Technology, 2004, 93, 119-123.*
Rocha et al, Applied Catalysis A: General, 2009, 352, 188-192.*
International Search Report of International Application No. PCT/MY2014/000050 completed and dated Sep. 8, 2014 (4 pages).
Written Opinion of International Application No. PCT/MY2014/000050 completed and dated Sep. 8, 2014 (5 pages).
W. Yu et al, Determination of Adsorption and Kinetic Parameters for Methyl Acetate Esterification and Hydrolysis Reaction Catalyzed by Amberlyst 15, Applied Catalysis A: General 260 (2004), pp. 191-205.
C.M. Zhang et al, Isobutene Hydration over Amberlyst-15 in a Slurry Reactor, Chemical Engineering and Processing 42 (2003), pp. 985-991.
J.H. Badia et al, Simultaneous Etherification of Isobutene with Ethanol and 1-Butanol over Ion-Exchange Resins, Applied Catalysis A, General 541 (2017), pp. 141-150.

* cited by examiner
† cited by third party

*Primary Examiner* — Ganapathy Krishnan
(74) *Attorney, Agent, or Firm* — Pyprus Pte Ltd

(57) ABSTRACT

Various ingredients and compositions are prepared from *Stevia rebaudiana* Bertoni plant. The compositions can be used as bulking agents, and sweeteners in foods, beverages, cosmetics and pharmaceuticals.

2 Claims, 5 Drawing Sheets

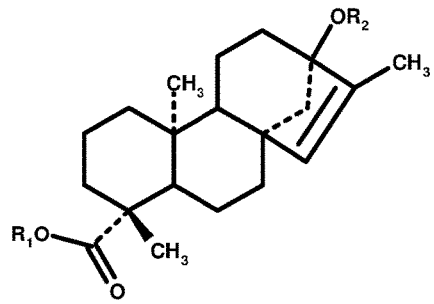

| Formula # | Compound Name | R₁ | R₂ |
|---|---|---|---|
| 1 | iso-Rubusoside | Glcβ1- | Glcβ1- |
| 2 | iso-Steviolbioside | H | Glcβ(1-2)Glcβ1- |
| 3 | iso-Stevioside | Glcβ1- | Glcβ(1-2)Glcβ1- |
| 4 | Unnamed 1 | Glcβ(1-2)Glcβ1- | Glcβ1- |
| 5 | iso-Rebaudioside E | Glcβ(1-2)Glcβ1- | Glcβ(1-2)Glcβ1- |
| 6 | iso-Rebaudioside B | H | Glcβ(1-2)[Glcβ(1-3)]Glcβ1- |
| 7 | DAQ3 | Glcβ1- | Glcβ(1-2)[Glcβ(1-3)]Glcβ1- |
| 8 | iso-Rebaudioside D | Glcβ(1-2)Glcβ1- | Glcβ(1-2)[Glcβ(1-3)]Glcβ1- |
| 9 | iso-Rebaudioside I | Glcβ(1-3)Glcβ1- | Glcβ(1-2)[Glcβ(1-3)]Glcβ1- |
| 10 | iso-Rebaudioside G | Glcβ1- | Glcβ(1-3)Glcβ1- |
| 11 | iso-Rebaudioside M | Glcβ(1-2)[Glcβ(1-3)]Glcβ1- | Glcβ(1-2)[Glcβ(1-3)]Glcβ1- |
| 12 | Unnamed 2 | Glcβ1- | Glcβ(1-6)Glcβ(1-2)Glcβ1- |
| 13 | iso-Rebaudioside L | Glcβ1- | Glcβ(1-6)Glcβ(1-2)[Glcβ(1-3)]Glcβ1- |
| 14 | iso-Dulcoside A | Glcβ1- | Rhaα(1-2)Glcβ1- |
| 15 | iso-Dulcoside B | H | Rhaα(1-2)[Glcβ(1-3)]Glcβ1- |
| 16 | iso-Rebaudioside C | Glcβ1- | Rhaα(1-2)[Glcβ(1-3)]Glcβ1- |
| 17 | iso-Rebaudioside H | Glcβ1- | Glcβ(1-3)Rhaα(1-2)[Glcβ(1-3)]Glcβ1- |
| 18 | iso-Rebaudioside K | Glcβ(1-2)Glcβ1- | Rhaα(1-2)[Glcβ(1-3)]Glcβ1- |
| 19 | iso-Rebaudioside J | Rhaα(1-2)Glcβ1- | Glcβ(1-2)[Glcβ(1-3)]Glcβ1- |
| 20 | iso-Rebaudioside N | Rhaα(1-2)[Glcβ(1-3)]Glcβ1- | Glcβ(1-2)[Glcβ(1-3)]Glcβ1- |
| 21 | iso-Rebaudioside O | Glcβ(1-3)Rhaα(1-2)[Glcβ(1-3)]Glcβ1- | Glcβ(1-2)[Glcβ(1-3)]Glcβ1- |
| 22 | Unnamed 3 | Glcβ1- | Xylβ(1-2)Glcβ1- |
| 23 | iso-Rebaudioside F | Glcβ1- | Xylβ(1-2)[Glcβ(1-3)]Glcβ1- |
| 24 | Unnamed 4 | Glcβ1- | Glcβ(1-2)[Xylβ(1-3)]Glcβ1- |
| 25 | Unnamed 5 | Xylβ(1-6)Glcβ1- | Glcβ(1-2)Glcβ1- |
| 26 | Unnamed 6 | Glcβ1- | Glcβ(1-2)[Fruβ(1-3)]Glcβ1- |
| 27 | Unnamed 7 | Glcα(1-2)Glcα(1-4)Glcβ1- | Glcβ(1-2)Glcβ1- |
| 28 | Unnamed 8 | Glcβ1- | Glcα(1-3)Glcβ(1-2)[Glcβ(1-3)]Glcβ1- |
| 29 | Unnamed 9 | Glcβ1- | Glcα(1-4)Glcβ(1-2)[Glcβ(1-3)]Glcβ1- |
| 30 | Unnamed 10 | Glcβ1- | 6-deoxyGlcβ(1-2)Glcβ1- |
| 31 | Unnamed 11 | Glcβ1- | 6-deoxyGlcβ(1-2)[Glcβ(1-3)]Glcβ1- |
| 32 | Unnamed 12 | 6-deoxyGlcβ1- | Glcβ(1-2)[Glcβ(1-3)]Glcβ1- |

FIG 3

COMPOUNDS PRODUCED FROM STEVIA AND PROCESS FOR PRODUCING THE SAME

FIELD OF THE INVENTION

The invention relates to a process for producing compounds from the extract of the *Stevia rebaudiana* plant and further to the use of the produced compounds in various food products, beverages and other consumables.

BACKGROUND OF THE INVENTION

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* Bertoni produces a number of diterpene glycosides which feature high intensity sweetness and sensory properties superior to that of many other high potency sweeteners.

The above-mentioned sweet glycosides have a common aglycon, steviol, and differ by the number and type of carbohydrate residues at the C13 and C19 positions. The leaves of Stevia are able to accumulate up to 10-20% (on dry weight basis) steviol glycosides. The major glycosides found in Stevia leaves are rebaudioside A (2-10%), stevioside (2-10%), and rebaudioside C (1-2%). Other glycosides such as rebaudioside B, D, E, and F, steviolbioside and rubusoside are found at much lower levels (approx. 0-0.2%).

Two major glycosides—stevioside and rebaudioside A (reb A), were extensively studied and characterized in terms of their suitability as commercial high intensity sweeteners. Stability studies in carbonated beverages confirmed their heat and pH stability (Chang S. S., Cook, J. M. (1983) Stability studies of stevioside and rebaudioside A in carbonated beverages. *J. Agric. Food Chem.* 31: 409-412.)

Steviol glycosides differ from each other not only by molecular structure, but also by their taste properties. Usually stevioside is found to be 110-270 times sweeter than sucrose, rebaudioside A between 150 and 320 times, and rebaudioside C between 40-60 times sweeter than sucrose. Dulcoside A is 30 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweetners. Pure Appl. Chem. 69:675-683; Phillips K. C. (1989) *Stevia*: steps in developing a new sweetener. In: Grenby T. H. ed. Developments in sweeteners, vol. 3. Elsevier Applied Science, London. 1-43.) The chemical structure of rebaudioside A is shown in FIG. 1.

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845.

However, even in a highly purified state, steviol glycosides still possess undesirable taste attributes such as bitterness, sweet aftertaste, licorice flavor, etc. One of the main obstacles for the successful commercialization of *stevia* sweeteners are these undesirable taste attributes. It was shown that these flavor notes become more prominent as the concentration of steviol glycosides increases (Prakash I., DuBois G. E., Clos J. F., Wilkens K. L., and Fosdick L. E. (2008) Development of rebiana, a natural, non-caloric sweetener. Food Chem. Toxicol., 46, S75S82).

Iso-Rebaudioside A (i.e., DAQ3) is one of the sweet glycosides found in *Stevia rebaudiana* (Cls J. F., Dubois G. E., and Prakash I. (2008) Photostability of Rebaudioside A and Stevioside in Beverages. *J. Agric. Food Chem.*, vol. 56, pp. 8507-13; Chaturvedula V. S. P., and Prakash I. (2011) Structure elucidation of three new diterpene glycosides from *Stevia rebaudiana*. *Int. J. Phys. Sci.*, vol. 6(29), pp. 6698-6705; Ceunen S., and Geuns J. M. C. (2013) Steviol Glycosides: Chemical Diversity, Metabolism, and Function. *J. Nat. Prod.*, vol. 76, pp. 1201-1228). The chemical structure of DAQ3 is shown in FIG. 2.

Only a few methods are described in the literature for preparing DAQ3.

U.S. Pat. No. 8,158,181 describes a process of preparing DAQ3 through isomerisation of reb A by incubation of reb A in an acid solution for more than two days. The DAQ3 was purified from obtained reaction media by silicagel chromatography. The described process might be suitable for laboratory scale preparation of DAQ3, but is hardly suitable for any large scale or commercial DAQ3 preparation.

Kobayashi et al. (1977) describe method of preparing compounds, with structure similar to DAQ3, by treating glucosidic compounds of *stevia* with weak acid and subsequently purifying on silicagel column (Kobayashi M., Horikawa S., Degrandi I. H., Ueno J., and Mitsuhashi H. (1977) Dulcosides A and B, new diterpene glycosides from *Stevia rebaudiana*. *Phytochemistry*, vol. 16, pp. 1405-08). Again the described process might be suitable for laboratory scale preparation of DAQ3, but is hardly suitable for any large scale or commercial DAQ3 preparation.

Chaturvedula and Prakash (2011) isolate DAQ3 from *Stevia rebaudiana* leaf extract by preparative HPLC method using a Phenomenex Prodigy ODS (3) column (5 μm; 250×21.2 mm).

It can be concluded that currently available methods for isolating and preparing DAQ3 are not suitable for feasible commercial production, and to date there is no supplier producing and offering DAQ3 on commercial scale.

Within the description of this invention we will show that, it is possible to feasibly produce DAQ3 and other similar glycosides on commercial scale. The produced DAQ3 and other similar glycosides can be used in various food products, beverages and other consumables as sweeteners, flavors, sweetness and flavor modifiers and/or enhancers etc.

SUMMARY OF THE INVENTION

The present invention is aimed to overcome the disadvantages of existing Stevia sweeteners. The invention describes a process for producing compounds from the extract of the *Stevia rebaudiana* plant and the use of the produced compounds in various food products and beverages as sweeteners, flavors, sweetness and flavor modifiers and/or enhancers.

The invention, in part, pertains to compounds comprising modified steviol glycosides of *Stevia rebaudiana* plant. The steviol glycosides are selected from the group consisting of: stevioside, rebaudioside A, rebaudioside B, rebaudioside C, rebaudioside D, rebaudioside E, rebaudioside F, rebaudioside M, rebaudioside N, rebaudioside O, dulcoside A, steviolbioside, rubusoside, glycosyl steviol glycosides, glucosyl steviol glycosides, enzymatically modified steviol glycosides, as well as other steviol glycosides found in *Stevia rebaudiana* plant and/or combinations thereof.

The invention, in part, pertains to a process of producing modified steviol glycosides from *Stevia rebaudiana* plant. The steviol glycosides are selected from the group consisting of: stevioside, rebaudioside A, rebaudioside B, rebaudioside C, rebaudioside D, rebaudioside E, rebaudioside F, rebaudioside M, rebaudioside N, rebaudioside O, dulcoside A, steviolbioside, rubusoside, glycosyl steviol glycosides, glucosyl steviol glycosides, enzymatically modified steviol glycosides, as well as other steviol glycosides found in *Stevia rebaudiana* plant and/or combinations thereof.

In the present invention, rebaudioside A product commercialized by PureCircle Sdn. Bhd. (Malaysia), containing, rebaudioside A (about 95-100%), stevioside (about 0-1%), rebaudioside C (about 0-1%), rebaudioside F (about 0-1%), rebaudioside B (about 0.1-0.8%), rebaudioside D (about 0-1%), and other glycosides amounting to total steviol glycosides' content of at least 95%, was used as a starting material. In addition, *stevia* extracts with different ratio and concentration of steviol glycosides may be used as starting materials. Non-limiting examples of the steviol glycosides include: stevioside, rebaudioside A, rebaudioside B, rebaudioside C, rebaudioside D, rebaudioside E, rebaudioside F, rebaudioside M, rebaudioside N, rebaudioside O, dulcoside A, steviolbioside, rubusoside, as well as other steviol glycosides found in *Stevia rebaudiana* plant and/or combinations thereof. Also enzymatically modified steviol glycosides such as glycosylated steviol glycosides or glucosylated steviol glycosides can be used.

The starting material is subjected to partial or complete conversion into DAQ3 and other modified steviol glycosides in aqueous alcohol or aqueous media.

Unlike the methods described in prior art (e.g. U.S. Pat. No. 8,158,181), the obtained reaction mixture, containing DAQ3 and other modified steviol glycosides, is substantially free from mineral compounds such as salts, acids etc, which significantly simplifies the further purification of DAQ3 and other modified steviol glycosides.

The obtained modified glycoside mixtures could be used "as-is". Alternatively, the DAQ3 or other modified steviol glycosides were purified and then used as pure ingredients.

The obtained products were applied in various foods, beverages and other consumables as sweeteners, flavors, sweetener enhancers, flavor enhancers, sweetener modifiers, flavor modifiers, including but not limited to soft drinks, ice cream, cookies, bread, fruit juices, milk products, baked goods and confectionary products.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 3 shows the general chemical structures of isomerized steviol glycosides.

DETAILED DESCRIPTION OF THE INVENTION

Figure 1:
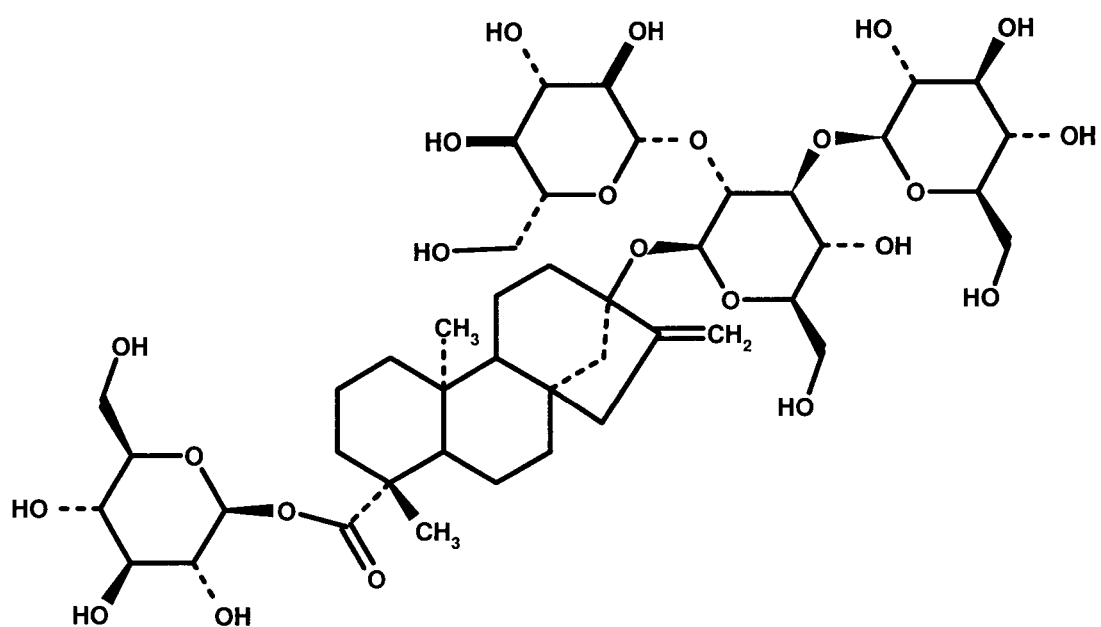
FIG. 1 shows the chemical structure of rebaudioside A.
Figure 2:
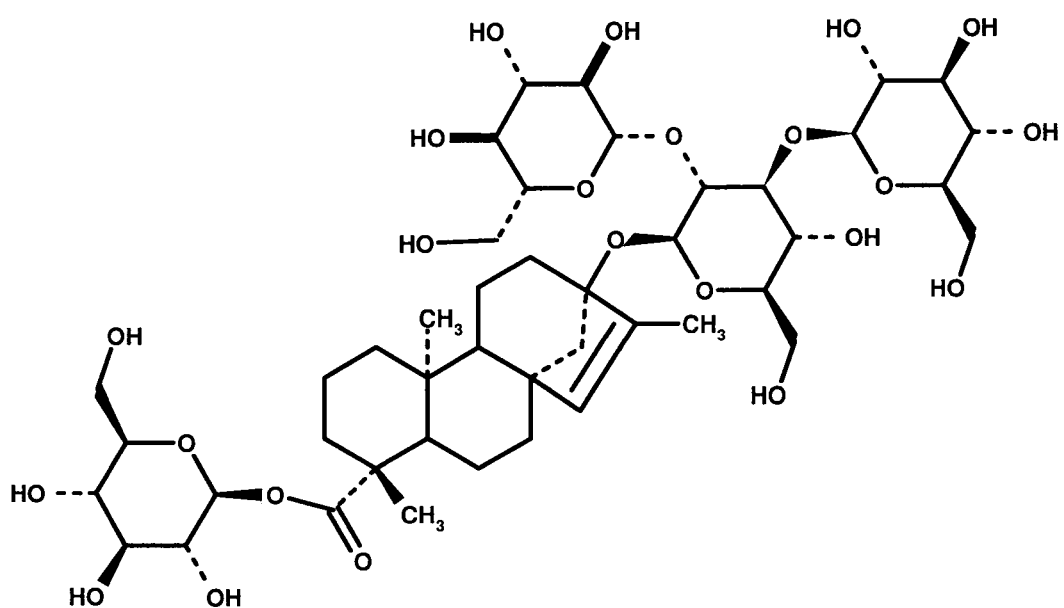
FIG. 2 shows the chemical structure of DAQ3.
Figure 4:
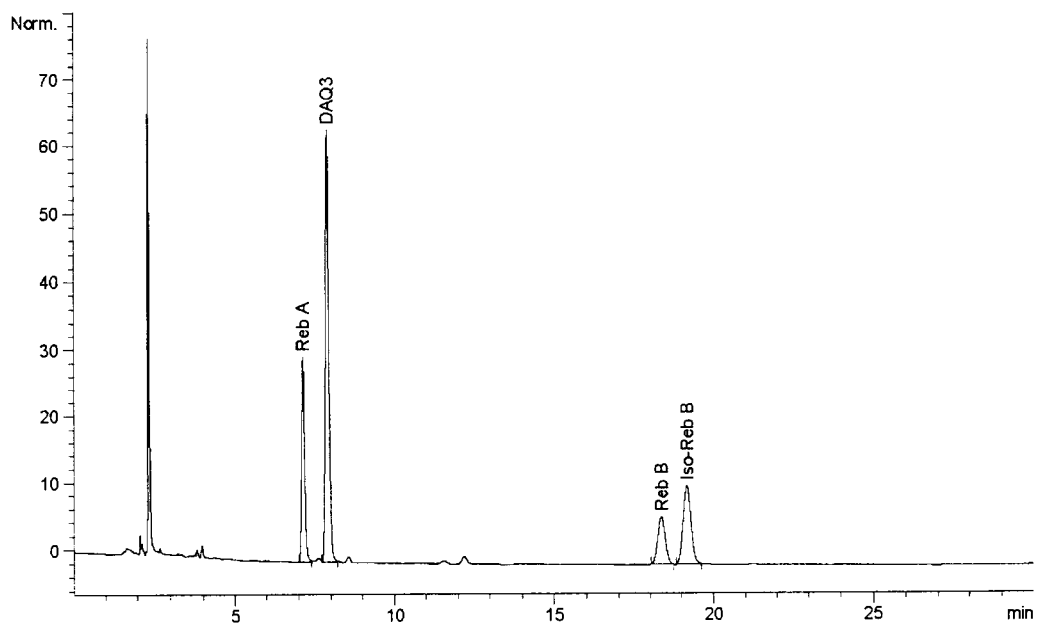
FIG. 4 shows a HPLC chromatogram of a reaction mixture containing DAQ3.
Figure 5:
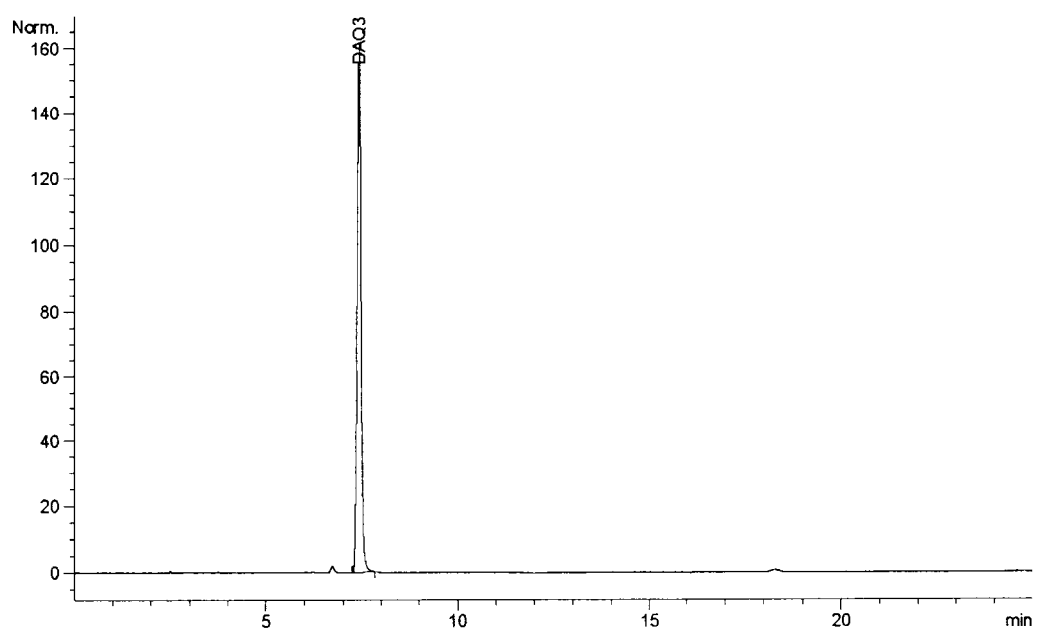
FIG. 5 shows a HPLC chromatogram of purified DAQ3.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In one aspect, the present invention provides a process of isomerizing reb A and other steviol glycosides. Briefly, the inventors of the present invention discovered that reb A and other steviol glycosides could be isomerized when contacted with ion-exchange resins in water or aqueous alcohol solutions.

Rebaudioside A product commercialized by PureCircle Sdn. Bhd. (Malaysia), containing, rebaudioside A (about 95-100%), stevioside (about 0-1%), rebaudioside C (about 0-1%), rebaudioside D (about 0-1%), rebaudioside F (about 0-1%), rebaudioside B (about 0.1-0.8%) and other glycosides amounting to total steviol glycosides' content of at least about 95%, was used as a starting material. In addition, stevia extracts with different ratio of steviol glycosides may be used as starting materials.

It is also to be noted that the process of the present invention is also applicable for isomerization of other glycosides of steviol such as stevioside, rebaudioside B, rebaudioside C, rebaudioside D, rebaudioside E, rebaudioside F, rebaudioside M, rebaudioside N, rebaudioside O, dulcoside A, steviolbioside, rubusoside, other steviol glycosides found in *Stevia rebaudiana* plant, glycosylated steviol glycosides, glucosylated steviol glycosides, enzymatically modified steviol glycosides and/or combinations thereof. The structures of isomers of exemplary glycosides are provided in FIG. 3.

The HPLC analysis of the raw materials and products was performed on an Agilent Technologies 1200 Series (USA) liquid chromarograph, equipped with Phenomenex Prodigy ODS3, 3 mm (4.6×250 mm) column at 55° C. The mobile phase was 32:68 mixture of acetonitrile and 10 mmol/L sodium phosphate buffer (about pH 2.6) at 1 mL/min. A diode array detector set at 210 nm was used as the detector. The reference standards of DAQ3 and iso-stevioside were obtained from Chromadex Inc., USA (Part #00009518 and #00009595).

In one embodiment of the present invention, reb A product was dissolved in water or aqueous alcohol solution. The concentration of reb A is about 0.001-50% (w/v) preferably about 1-10%. The preferred alcohols include methanol, ethanol, n-propanol, iso-propanol, butanol and/or mixtures thereof. Other solvents capable of dissolving the raw material, including pure water, may be used as well. The water to alcohol ratio in aqueous alcohol (vol./vol.) was in the range from 0.001%:99.999% to 99.999%:0.001%, preferably from about 40%:60% to 60%:40%. The pH of the prepared solution was in the range from pH 0 to pH 14, preferably from pH 6 to pH 8, more preferably neutral. The dissolved reb A product was contacted with ion-exchange resin at about 10-150° C., preferably about 30-100° C., for a period of about 0.5-48 hrs, preferably about 1-24 hrs. As a result reb A is completely or partially isomerized to DAQ3. Various process equipment known to art, which are capable of facilitating the contact of a liquid with ion-exchange resin can be used for this purpose. Non-limiting examples include: columns, reactors, vessels, tanks, simulated moving bed systems, continuous ion-exchange systems, chromatography systems, etc. Different equipments can be combined, and systems including multiple numbers of same equipment, connected in parallel or consecutively, can be use as well. The process can be conducted in one or several stages. The process can be run in batch, semi-batch, fed-batch and continuous modes. Preferably the process is conducted in continuous mode by using columns packed with ion-exchange resin.

In one embodiment the reb A product-dissolved solution is circulated through a column system packaged with ion-exchange resin until the desired level of DAQ3 is achieved.

In another embodiment the reb A product-dissolved solution is fed to a column system packaged with ion-exchange resin with at a rate sufficient to achieve the desired level of DAQ3 at the outlet of the system.

Various ion-exchange resins known to art can be used. Resins with various chemistry including acrylic, methacrylic, (linked with a di-functional monomer e.g. DVB), sulfonated copolymers of styrene and DVB, gel, microporous and macroporous, or mixtures thereof can be used. Weak or strong ion-exchange resins can be used. Weak or strong cation exchange resins can be used; preferably strong protonated cation exchange resin.

After contacting the reb A product-dissolved solution with ion-exchange resin a reaction mixture containing at least 1 mg/L of DAQ3 is obtained. Preferably the reaction medium is containing from 10,000 mg/L to 500,000 mg/L DAQ3.

In one embodiment the DAQ3 is crystallized from the obtained reaction mixture.

In one embodiment the DAQ3 is crystallized from the obtained reaction mixture containing 0.001% to 90% total solids, preferably 1% to 50% total solids.

In another embodiment the DAQ3 is crystallized from reaction mixture after addition of at least one other solvent.

In yet another embodiment the DAQ3 is crystallized from reaction mixture after removal of at least one of the solvents.

In one embodiment the pH of the reaction mixture is adjusted to pH 7.0 to pH 14.0, preferably pH 8 to pH 10 before crystallization of DAQ3.

In yet another embodiment the crystallization of DAQ3 is induced by addition of DAQ3 crystals as a starter.

In another embodiment the crystallization of DAQ3 is induced without addition of DAQ3 crystals.

In one embodiment the crystallization is repeated at least one time.

In another embodiment at least one step of crystallization is conducted in media comprising water from 0.0001% to 99.999% (vol./vol.) and at least one organic solvent from 0.0001% to 99.999% (vol./vol.).

In one embodiment the DAQ3 purification process includes at least one step of chromatographic purification by any chromatographic separation method known to art.

In another method the DAQ3 purification process includes at least one membrane filtration step using any type of membrane known to art.

In one embodiment the DAQ3 crystals were separated by any method known in the art such as filtration, centrifugation etc.

In one embodiment the DAQ3 crystals were dried by different drying methods, including but not limited to vacuum drying, belt vacuum drying, oven drying, microwave drying, fluid bed drying, spray drying, flash drying, freeze drying etc.

In yet another embodiment the DAQ3 powder particle size was adjusted by pulverization, granulation, agglomeration or any other method known to art to produce particles from 0.00001μ m to 10 mm.

In yet another embodiment the DAQ3 crystals were subjected to various treatments by different chemical and physical agents know to art to yield various polymorphic forms, including amorphous forms.

In one particular embodiment, after the reaction, the alcohol was removed from the solution, and the aqueous solution was concentrated to about 1% to 90% total solids content. The pH of the solution was adjusted to pH 9 to pH 10 and the DAQ3 was crystallized during 24 hrs. The DAQ3 crystals were separated by filtration to produce first crystals. The obtained first crystals were dried under vacuum at about 60-105° C. to yield a glycoside mixture comprising DAQ3 about 5-95%, preferably about 10-95%, and more preferably about 30-90%.

In embodiment, after the reaction, the reaction mixture was dried. The dried powder was dispersed or dissolved in water or aqueous alcohol, the pH of the solution was adjusted to pH 9 to pH 10 and the DAQ3 was crystallized during 24 hrs. The ratio of the dried powder to water (wt/vol) or aqueous alcohol was from 1:1 to 1:10. The DAQ3 crystals were separated by filtration to produce first crystals. The obtained first crystals were dried under vacuum at about 60-105° C. to yield a glycoside mixture comprising DAQ3 about 5-95%, preferably about 10-95%, and more preferably about 30-90%.

In another embodiment, the first crystals were suspended in water, the pH of the mixture was adjusted to pH 9 to pH 10, and the mixture is subjected to continuous agitation over about 0.5-24 hrs, preferably about 1-3 hours, at about 50-100° C., preferably about 10-60° C. The ratio of the first crystals to water (wt/vol) was from 1:1 to 1:10. The DAQ3 crystals were separated by filtration to produce second crystals. The obtained second crystals were dried under vacuum at about 60-105° C. to yield a glycoside mixture comprising DAQ3 about 50-99%, preferably about 70-98, and more preferably about 80-97%.

In another embodiment, the first crystals were dissolved in water to produce a solution with about 1-90% total solids content. The pH of the solution was adjusted to pH 9 to pH 10, and the solution was subjected to continuous agitation over about 0.5-24 hrs, preferably about 16-22 hours, at about 5-100° C., preferably about 10-30° C. The DAQ3 crystals were separated by filtration to produce second crystals. The obtained second crystals were dried under vacuum at about 60-105° C. to yield a glycoside mixture comprising DAQ3 about 50-99%, preferably about 70-98%, and more preferably about 80-97%

In another embodiment, the first crystals were dissolved in aqueous alcohol to produce a solution with about 1-90% total solids content. The preferred alcohols include methanol, ethanol, n-propanol, iso-propanol, butanol and/or mixtures thereof, however other solvents capable of dissolving the first crystals, including pure alcohols, may be used as well. The water to alcohol ratio in aqeous alcohol (vol./vol.) was in the range from 0.001%:99.999% to 99.999%: 0.001%, preferably from about 1%:99% to 50%:50%. The pH of the solution was adjusted to pH 9 to pH 10, and the solution was subjected to continuous agitation over about 0.5-24 hrs, preferably about 16-22 hours, at about 5-100° C., preferably about 10-30° C. The DAQ3 crystals were separated by filtration to produce second crystals. The obtained second crystals were dried under vacuum at about 60-105°

C. to yield a glycoside mixture comprising DAQ3 about 50-99%, preferably about 70-98%, and more preferably about 80-97%.

In another embodiment, the second crystals were dissolved in water or aqueous alcohol to produce a solution with about 1-90% total solids content. The pH of the mixture was adjusted to pH 9 to pH 10, and the solution was subjected to continuous agitation over about 0.5-24 hrs, preferably about 16-22 hours, at about 5-100° C., preferably about 10-30° C. The DAQ3 crystals were separated by filtration to produce third crystals. The obtained third crystals were dried under vacuum at about 60-105° C. to yield a glycoside mixture comprising of DAQ3 with purity of >99%.

The compositions can be used as sweetener, flavor, sweetness enhancer, flavor enhancer, sweetness modifier, flavor modifier in various food and beverage products at the concentration from 0.1 ppm to 999,999 ppm. Non-limiting examples of food and beverage products include carbonated soft drinks, ready to drink beverages, energy drinks, isotonic drinks, low-calorie drinks, zero-calorie drinks, sports drinks, sodas, colas, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like, at the concentration from 0.1 ppm to 999,999 ppm.

The obtained compositions can be used "as-is" or in combination with other sweeteners, flavors and food ingredients.

Non-limiting examples of sweeteners include at least one sweetener selected from group including steviol glycosides, stevioside, rebaudioside A, rebaudioside B, rebaudioside C, rebaudioside D, rebaudioside E, rebaudioside F, rebaudioside M, rebaudioside N, rebaudioside O, dulcoside A, steviolbioside, rubusoside, glycosylated steviol glycosides, glucosylated steviol glycosides, enzymatically modified steviol glycosides as well as other steviol glycosides found in *Stevia rebaudiana* plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include at least one flavor selected from the group including lemon, orange, berry, fruit, banana, grape, pear, pineapple, bitter almond, cola, cinnamon, sugar, cotton candy, vanilla flavors, terpenoid glycosides and/or combinations thereof.

Non-limiting examples of other food ingredients include at least one selected from group of flavors, acidulants, organic acids, amino acids, coloring agents, bulking agents, modified starches, gums, texturizers, preservatives, antioxidants, emulsifiers, stabilisers, thickeners, gelling agents and/or combinations thereof.

It is to be understood that the process described in the invention can be used for preparing similar compounds from other steviol glycosides. Non limiting examples of these steviol glycosides include: stevioside, rebaudioside A, rebaudioside B, rebaudioside C, rebaudioside D, rebaudioside E, rebaudioside F, rebaudioside M, rebaudioside N, rebaudioside O, dulcoside A, steviolbioside, rubusoside, glycosylated steviol glycosides, glucosylated steviol glycosides, enzymatically modified steviol glycosides as well as other steviol glycosides found in *Stevia rebaudiana* plant and/or combinations thereof.

The following examples illustrate various embodiments of the invention. It will be understood that the invention is not limited to the materials, proportions, conditions and procedures set forth in the examples, which are only illustrative.

Example 1

Preparation of Stevia Sweetener 80 g of rebaudioside A produced by PureCircle Sdn. Bhd. (Malaysia), containing, 98.3% rebaudioside A, 0.1% stevioside, 0.1% rebaudioside C, 0.2% rebaudioside F, 0.4% rebaudioside B, 0.2% DAQ3, and 0.5% rebaudioside D was dissolved in 50%:50% (vol./vol.) blend of absolute ethanol and ultrapure water to make 4,000 mL solution. The solution was fed to a 250 mL jacketed column packed with protonated cation exchange resin (Amberlite™ IR120, Rohm and Haas USA). The column temperature was maintained at 50° C. After 24 hrs the solution was assayed by HPLC. The solution contained (on dry anhydrous basis) 20.9% rebaudioside A, 11.3% rebaudioside B, 47.8% DAQ3, 19.9% iso-Reb B and traces of other glycosides. The solution was evaporated to remove ethanol and the remaining aqueous solution (pH 5) was diluted with water to about 2% total solids content. The pH was adjusted by NaOH to pH 10 and the solution was agitated at room temperature for about 24 hrs. The precipitated crystals were separated, dried under vacuum to yield about 30 g first crystals. HPLC assay show the first crystals contain (on dry anhydrous basis) 3.1% rebaudioside A, 0.7% rebaudioside B, 80.4% DAQ3, 15.5% iso-Reb B and traces of other glycosides.

Example 2

Preparation of Stevia Sweetener by Acid Treatment 80 g of rebaudioside A produced by PureCircle Sdn. Bhd. (Malaysia), containing, 98.3% rebaudioside A, 0.1% stevioside, 0.1% rebaudioside C, 0.2% rebaudioside F, 0.4% rebaudioside B, 0.2% DAQ3, and 0.5% rebaudioside D was dissolved in ultrapure water to make 4,000 mL solution. The pH was adjusted to pH 2.0 by phosphoric acid and the solution was incubated at 50° C. for 7 days. After 1 day and 7 days the solution was analyzed by HPLC. The 1 day solution contained (on dry anhydrous basis) 90.4% rebaudioside A, 1.7% rebaudioside B, 5.1% DAQ3, 1.2% iso-Reb B and traces of other glycosides. The 7 day solution contained (on dry anhydrous basis) 38.9% rebaudioside A, 11.2% rebaudioside B, 40.9% DAQ3, 9.0% iso-Reb B and traces of other glycosides. The solution was diluted to about 2% total solids and the pH was adjusted by NaOH to pH 10. The solution was agitated at room temperature for about 24 hrs. The precipitated crystals were separated, dried under vacuum to yield about 22 g crystals. HPLC assay show the crystals contain (on dry anhydrous basis) 22.9% rebaudioside A, 6.2% rebaudioside B, 66.1% DAQ3, 4.1% iso-Reb B and traces of other glycosides.

Example 3

Preparation of Stevia Sweetener 80 g of rebaudioside A produced by PureCircle Sdn. Bhd. (Malaysia), containing, 98.3% rebaudioside A, 0.1% stevioside, 0.1% rebaudioside C, 0.2% rebaudioside F, 0.4% rebaudioside B, 0.2% DAQ3, and 0.5% rebaudioside D was dissolved in 50%:50% (vol./vol.) blend of absolute ethanol and ultrapure water to make 4,000 mL solution. The solution was mixed with 250 mL protonated cation exchange resin (Amberlite™ IR120, Rohm and Haas USA) in a jacketed reactor. The mixture temperature was maintained at 50° C. After 24 hrs the resin was separated from solution by filtration. The obtained solution was assayed by HPLC. The solution contained (on dry anhydrous basis) 20.1% rebaudioside A, 12.4% rebaudioside B, 45.9% DAQ3, 21.6% iso-Reb B and traces of other glycosides. The solution was evaporated to remove ethanol and the remaining aqueous solution (pH 5) was diluted with water to about 2% total solids content. The pH was adjusted by NaOH to pH 10 and the solution was agitated at room temperature for about 24 hrs. The precipitated crystals were separated, dried under vacuum to yield about 28 g first crystals. HPLC assay show the first crystals contain (on dry anhydrous basis) 3.8% rebaudioside A, 1.0% rebaudioside B, 79.1% DAQ3, 16.1% iso-Reb B and traces of other glycosides.

Example 4

Preparation of Stevia Sweetener 50 g of first crystals prepared according to EXAMPLE 1 were dissolved in ultrapure water to make 2,500 mL solution. The pH was adjusted by NaOH to pH 10 and the solution was agitated at room temperature for about 24 hrs. The precipitated crystals were dried under vacuum to yield about 35 g second crystals. HPLC assay show the second crystals contain (on dry anhydrous basis) 2.1% rebaudioside A, 0.3% rebaudioside B, 95.1% DAQ3, 2.5% iso-Reb B and traces of other glycosides. The procedure was repeated to produce about 27 g third crystals which contain (on dry anhydrous basis) 0.1% rebaudioside A, 0.2% rebaudioside B, 99.3% DAQ3, 0.5% iso-Reb B and traces of other glycosides.

Example 5

Preparation of Stevia Sweetener 80 g of stevioside produced by PureCircle Sdn. Bhd. (Malaysia), containing, 98.4% stevioside, 0.5% rebaudioside A, 0.3% rebaudioside C, 0.7% steviolbioside, and 0.1% iso-stevioside, was dissolved in 50%:50% (vol./vol.) blend of absolute ethanol and ultrapure water to make 4,000 mL solution. The solution was fed to a 250 mL jacketed column packed with protonated cation exchange resin (Amberlite™ IR120, Rohm and Haas USA). The column temperature was maintained at 50° C. After 24 hrs the solution was assayed by HPLC. The solution contained (on dry anhydrous basis) 25.1% stevioside, 10.5% steviolbioside, 46.6% iso-stevioside, 17.8% iso-steviolbioside and traces of other glycosides. The solution was evaporated to remove ethanol and the remaining aqueous solution (pH 5) was diluted with water to about 2% total solids content. The pH was adjusted by NaOH to pH 10 and the solution was agitated at room temperature for about 24 hrs. The precipitated crystals were separated, dried under vacuum to yield about 29 g crystals. HPLC assay show the crystals contain (on dry anhydrous basis) 2.7% stevioside, 1.0% steviolbioside, 83.1% iso-stevioside, 13.2% iso-steviolbioside and traces of other glycosides. These crystals were dissolved in ultrapure water to make 5% solution. The pH was adjusted by NaOH to pH 10 and the solution was agitated at room temperature for about 24 hrs. The precipitated crystals were dried under vacuum to yield about 20 g crystals. The procedure was repeated to produce about 18 g crystals which contain (on dry anhydrous basis) 0.1% stevioside, 0.4% steviolbioside, 99.0% iso-stevioside, 0.5% iso-steviolbioside and traces of other glycosides.

Example 6

Zero-Calorie Carbonated Beverage

Carbonated beverages according to formula presented in Table 1 below were prepared.

TABLE 1

Formula for carbonated beverages

| | Quantity, % | | |
|---|---|---|---|
| Ingredients | Stevia Extract | Reb A | EXAMPLE 4 |
| Cola flavor | 0.340 | 0.340 | 0.340 |
| ortho-Phosphoric acid | 0.100 | 0.100 | 0.100 |
| Sodium citrate | 0.310 | 0.310 | 0.310 |
| Sodium benzoate | 0.018 | 0.018 | 0.018 |
| Citric acid | 0.018 | 0.018 | 0.018 |
| Stevia composition | 0.050 | 0.050 | 0.050 |
| Carbonated water | to 100 | to 100 | to 100 |

The sensory properties were evaluated by 20 panelists. The results are summarized in Table 2.

TABLE 2

Evaluation of zero-calorie carbonated beverage samples

| | Number of panelists detected the attribute | | |
|---|---|---|---|
| Taste attribute | Stevia Extract | Reb A | EXAMPLE 4 |
| Bitter taste | 15 | 12 | 0 |
| Astringent taste | 16 | 10 | 1 |
| Aftertaste | 17 | 11 | 2 |
| Comments | | | |
| Quality of sweet taste | Bitter aftertaste (14 of 20) | Bitter aftertaste (10 of 20) | Clean (18 of 20) |
| Overall evaluation | Satisfactory (0 of 20) | Satisfactory (6 of 20) | Satisfactory (18 of 20) |

The above results showed that the beverages prepared using the composition obtained according to EXAMPLE 4 possessed the best organoleptic characteristics.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

I claim:

1. A process for producing an isomerized *stevia* compound, comprising the steps of:

(a) providing a steviol glycoside(s) composition;
(b) providing an aqueous alcohol solvent;
(c) dissolving the steviol glycosides composition in the solvent to produce steviol glycoside(s) solution; and
(d) contacting the steviol glycoside(s) solution with protonated cation exchange resin to produce the stevia compound solution containing at least 1%, on anhydrous basis, the isomerized stevia compound having the formula:

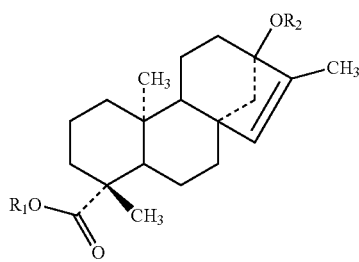

and being selected from one or more of the group consisting of:
(1) iso-Rubusoside, where $R_1$ is Glc.beta.1-, and $R_2$ is Glc.beta.1-;
(2) iso-Steviolbioside, where $R_1$ is H, and $R_2$ is Glc.beta.(1-2)Glc.beta.1-;
(3) iso-Stevioside, where $R_1$ is Glc.beta.1-, and $R_2$ is Glc.beta.(1-2)Glc.beta.1-;
(4) Isomerized steviol glycoside formula 4, where $R_1$ is Glc.beta.(1-2)Glc.beta.1-, and $R_2$ is Glc.beta.1-;
(5) iso-Rebaudioside E, where $R_1$ is Glc.beta.(1-2)Glc.beta.1-, and $R_2$ is Glc.beta.(1-2)Glc.beta.1-;
(6) iso-Rebaudioside B, where $R_1$ is H, and $R_2$ is Glc.beta.(1-2)[Glc.beta.(1-3)]Glc.beta.1-;
(7) DAQ3, where $R_1$ is Glc.beta.1-, and $R_2$ is Glc.beta.(1-2)[Glc.beta.(1-3)]Glc.beta.1-;
(8) iso-Rebaudioside D, where $R_1$ is Glc.beta.(1-2)Glc.beta.1-, and $R_2$ is Glc.beta.(1-2)[Glc.beta.(1-3)]Glc.beta.1-;
(9) iso-Rebaudioside I, where $R_1$ is Glc.beta.(1-3)Glc.beta.1-, and $R_2$ is Glc.beta.(1-2)[Glc.beta.(1-3)]Glc.beta.1-;
(10) iso-Rebaudioside G, where $R_1$ is Glc.beta.1-, and $R_2$ is Glc.beta.(1-3)Glc.beta.1-;
(11) iso-Rebaudioside M, where $R_1$ is Glc.beta.(1-2)[Glc.beta.(1-3)]Glc.beta.1-, and $R_2$ is Glc.beta.(1-2)[Glc.beta.(1-3)]Glc.beta.1-;
(12) Isomerized steviol glycoside formula 12, where $R_1$ is Glc.beta.1-, and $R_2$ is Glc.beta.(1-6)Glc.beta.(1-2)Glc.beta.1-;
(13) iso-Rebaudioside L, where $R_1$ is Glc.beta.1-, and $R_2$ is Glc.beta.(1-6)Glc.beta.(1-2)[Glc.beta.(1-3)]Glc.beta.1-;
(14) iso-Dulcoside A, where $R_1$ is Glc.beta.1-, and $R_2$ is Rha.alpha.(1-2)Glc.beta.1-;
(15) iso-Dulcoside B, where $R_1$ is H, and $R_2$ is Rha.alpha.(1-2)[Glc.beta.(1-3)]Glc.beta.1-;
(16) iso-Rebaudioside C, where $R_1$ is Glc.beta.1-, and $R_2$ is Rha.alpha.(1-2)[Glc.beta.(1-3)]Glc.beta.1-;
(17) iso-Rebaudioside H, where $R_1$ is Glc.beta.1-, and $R_2$ is Glc.beta.(1-3)Rha.alpha.(1-2)[Glc.beta.(1-3)]Glc.beta.1-;
(18) iso-Rebaudioside K, where $R_1$ is Glc.beta.(1-2)Glc.beta.1-, and $R_2$ is Rha.alpha.(1-2)[Glc.beta.(1-3)]Glc.beta.1-;
(19) iso-Rebaudioside J, where $R_1$ is Rha.alpha.(1-2)Glc.beta.1-, and $R_2$ is Glc.beta.(1-2)[Glc.beta.(1-3)]Glc.beta.1-;
(20) iso-Rebaudioside N, where $R_1$ is Rha.alpha.(1-2)[Glc.beta.(1-3)]Glc.beta.1-, and $R_2$ is Glc.beta.(1-2)[Glc.beta.(1-3)]Glc.beta.1-;
(21) iso-Rebaudioside O, where $R_1$ is Glc.beta.(1-3)Rha.alpha.(1-2)[Glc.beta.(1-3)]Glc.beta.1-, and $R_2$ is Glc.beta.(1-2)[Glc.beta.(1-3)]Glc.beta.1-;
(22) Isomerized steviol glycoside formula 22, where $R_1$ is Glc.beta.1-, and $R_2$ is Xyl.beta.(1-2)Glc.beta.1-;
(23) iso-Rebaudioside F, where $R_1$ is Glc.beta.1-, and $R_2$ is Xyl.beta.(1-2)[Glc.beta.(1-3)]Glc.beta.1-;
(24) Isomerized steviol glycoside formula 24, where $R_1$ is Glc.beta.1-, and $R_2$ is Glc.beta.(1-2)[Xyl.beta.(1-3)]Glc.beta.1-;
(25) Isomerized steviol glycoside formula 25, where $R_1$ is Xyl.beta.(1-6)Glc.beta.1-, and $R_2$ is Glc.beta.(1-2)Glc.beta.1-;
(26) Isomerized steviol glycoside formula 26, where $R_1$ is Glc.beta.1-, and $R_2$ is Glc.beta.(1-2)[Fru.beta.(1-3)]Glc.beta.1-;
(27) Isomerized steviol glycoside formula 27, where $R_1$ is Glc.alpha.(1-2)Glc.alpha.(1-4)Glc.beta.1-, and $R_2$ is Glc.beta.(1-2)Glc.beta.1-;
(28) Isomerized steviol glycoside formula 28, where $R_1$ is Glc.beta.1-, and $R_2$ is Glc.alpha.(1-3)Glc.beta.(1-2)[Glc.beta.(1-3)]Glc.beta.1-;
(29) Isomerized steviol glycoside formula 29, where $R_1$ is Glc.beta.1-, and $R_2$ is Glc.alpha.(1-4)Glc.beta.(1-2)[Glc.beta.(1-3)]Glc.beta.1-;
(30) Isomerized steviol glycoside formula 30, where $R_1$ is Glc.beta.1-, and $R_2$ is 6-deoxyGlc.beta.(1-2)Glc.beta.1-;
(31) Isomerized steviol glycoside formula 31, where $R_1$ is Glc.beta.1-, and $R_2$ is 6-deoxyGlc.beta.(1-2)[Glc.beta.(1-3)]Glc.beta.1-; and
(32) Isomerized steviol glycoside formula 32, where $R_1$ is 6-deoxyGlc.beta.1-, and $R_2$ is Glc.beta.(1-2)[Glc.beta.(1-3)]Glc.beta.1-.

2. The process of claim 1 further comprising the step(s) of:
(e) adjusting the pH of the isomerized stevia compound solution of step (d) to pH greater than 8.0; and
(f) crystallizing the stevia compound from the stevia compound solution of step (e) to produce crystals containing at least 50% on anhydrous basis of the isomerized stevia compound.

* * * * *